(12) United States Patent
Chou et al.

(10) Patent No.: US 11,243,201 B2
(45) Date of Patent: Feb. 8, 2022

(54) SAMPLE COLLECTION, HOLDING AND ASSAYING

(71) Applicant: Essenlix Corporation, Monmouth Junction, NJ (US)

(72) Inventors: Stephen Y. Chou, Princeton, NJ (US); Wei Ding, Princeton, NJ (US); Ji Li, Princeton, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 150 days.

(21) Appl. No.: 16/640,397

(22) PCT Filed: Aug. 1, 2018

(86) PCT No.: PCT/US2018/044775
§ 371 (c)(1),
(2) Date: Feb. 20, 2020

(87) PCT Pub. No.: WO2019/028123
PCT Pub. Date: Feb. 7, 2019

(65) Prior Publication Data
US 2020/0363409 A1    Nov. 19, 2020

Related U.S. Application Data

(60) Provisional application No. 62/539,691, filed on Aug. 1, 2017, provisional application No. 62/539,705, filed on Aug. 1, 2017.

(51) Int. Cl.
*G01N 1/00*     (2006.01)
*G01N 33/543*   (2006.01)
*G01N 1/28*     (2006.01)
*G01N 1/02*     (2006.01)

(52) U.S. Cl.
CPC ..... *G01N 33/54386* (2013.01); *G01N 1/2813* (2013.01); *G01N 2001/028* (2013.01)

(58) Field of Classification Search
None
See application file for complete search history.

(56) References Cited

U.S. PATENT DOCUMENTS

| 3,368,872 A | 2/1968 | Natelson |
| 3,447,863 A | 6/1969 | Patterson |
| 3,895,661 A | 7/1975 | Praglin et al. |
| 3,925,166 A | 12/1975 | Blume |

(Continued)

FOREIGN PATENT DOCUMENTS

| AU | 198813789 A | 9/1988 |
| AU | 619459 B    | 1/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

(Continued)

*Primary Examiner* — Jyoti Nagpaul

(57) ABSTRACT

The present invention provides devices, systems, and methods, for performing biological and chemical assays.

57 Claims, 7 Drawing Sheets

(56) References Cited

U.S. PATENT DOCUMENTS

| | | |
|---|---|---|
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |

(56) References Cited

U.S. PATENT DOCUMENTS

| | | |
|---|---|---|
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1* | 8/2010 | Wardlaw ............ G01N 1/2813 436/63 |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |

OTHER PUBLICATIONS

International Report on Patentability for PCT/US2018/037168 established by IPEA/US dated Aug. 19, 2019.

* cited by examiner

A

B

C

D

A

B

SAMPLE COLLECTION, HOLDING AND ASSAYING

CROSS-REFERENCE

This application is a National Stage entry (§ 371) application of International Application No. PCT/US2018/044775, filed on Aug. 1, 2018, which claims the benefit of U.S. Provisional Patent Application 62/539,691, filed Aug. 1, 2017, and U.S. Provisional Patent Application 62/539,705, filed Aug. 1, 2017, the contents of which are relied upon and incorporated herein by reference in their entirety.

The entire disclosure of any publication or patent document mentioned herein is entirely incorporated by reference.

BACKGROUND

In clinical diagnostic settings, a swab is often used to collect a sample from a human or non-human subject, for instance, when bodily fluids like nasal discharge or genital discharge are collected as the sample for bio/chemical assays. A swab is also often used in other settings as an easy-to-use tool for sample collection. However, conventionally testing techniques often require the transfer of the sample from the collecting swab to a liquid-based testing medium followed by the further transfer of the sample-containing testing medium into a testing device. Such a double-transfer process undesirably slows down the overall testing procedure, and requires transferring devices and often professional handling, thereby impeding the development of point-of-care and point-of-need testing of samples collected by a swab. In biological and chemical assays (e.g. diagnostic testing), it is often necessary to collect sample from a subject and transport and apply the sample to an assay device. Conventional devices and methods for sample collection and application are often hard to be adapted to miniaturized assays for point of care or personal use, and usually require professional handling.

The present disclosure provides, among many others, a solution to tackle these problems. The present disclosure provides kits, devices and methods for rapid, easy to use, and/or inexpensive testing of samples collected by a swab, eliminating the need of extra transferring devices and professional handling and offering a solution for point-of-care and point-of-need settings.

BRIEF DESCRIPTION OF THE DRAWINGS

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the present disclosure by way of example and not by way of limitation. If any, the section headings and any subtitles, if any, are for organizational purposes only and are not to be construed as limiting the subject matter described in any way. The contents under a section heading and/or subtitle are not limited to the section heading and/or subtitle, but apply to the entire description of the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It should be noted that the Figures do not intend to show the elements in strict proportion. For clarity purposes, some elements are enlarged when illustrated in the Figures. The dimensions of the elements should be delineated from the descriptions herein provided and incorporated by reference.

Test Kit and QMAX Device

One aspect of the present disclosure is to provide a kit for testing a sample collected by a swab.

Figure 1:
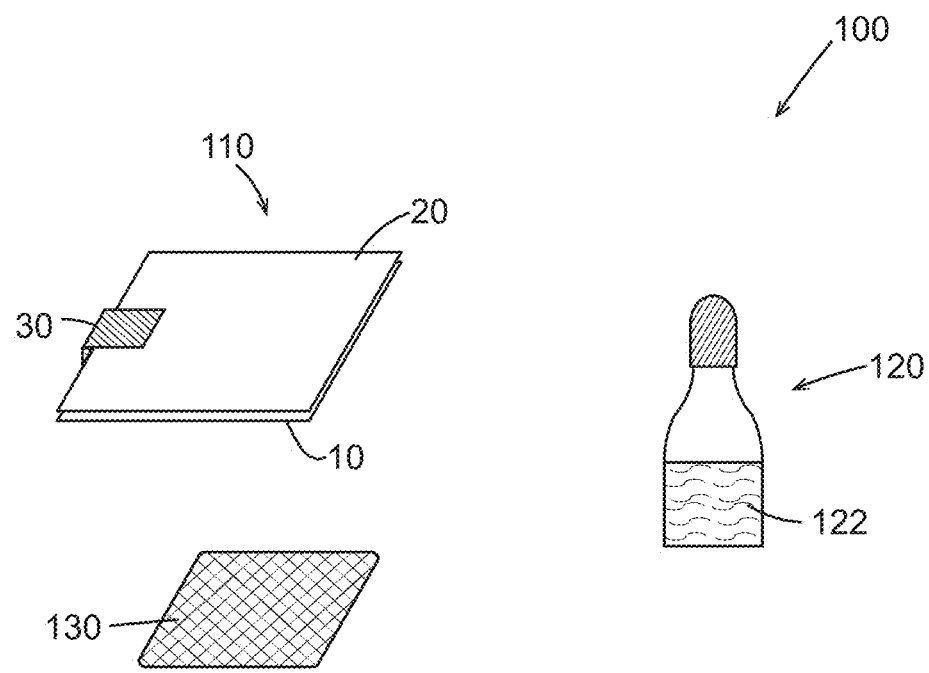
FIG. 1 shows an embodiment of the test kit of the present disclosure; the test kit includes a QMAX device that comprises a first plate and a second plate, a swab, and a medium container that contains testing medium.

FIG. 1 shows an embodiment of the test kit 100 of the present disclosure. As shown in FIG. 1, the test kit 100 may comprise: a QMAX device 110 that has a QMAX device 110, a swab 130, and a medium container 120 that contains testing medium 122.

The kit 100 of the present disclosure is used to collect sample or specimen and perform tests of the collected sample or specimen. In some embodiments, the kit is used for detecting a pathogenic disease or pathological condition in a subject. In some embodiments, the kit is used for monitoring the health condition in a subject. Here the term "subject" may refer to human or animal. In certain embodiments, the subject is a person.

As shown in FIG. 1, the QMAX device comprises a first plate 10, a second plate 20, and a hinge 30, wherein the first plate 10 and the second plate 20 are connected by a hinge 30 so that the two plates may pivot against each other. As shown in FIG. 1, the kit also comprises a swab 130, which is used to collect a sample or specimen from the subject. In some embodiments, the swab 130 is an absorbent pad or piece of material having variable shape and size. In some embodiments, the swab is made of absorbent material such as but not limited to filter papers, absorbent polymers (e.g. polypropylene and polymethysiloxan polyhydrate), sponge, cellulose fiber, desiccant, or a combination thereof. In certain embodiments, the swab is a cotton swab, which includes a small wad of cotton on or both ends of a rod.

In some embodiments, the swab 130 is a swab strip, which has a flat, paper-like body. In certain embodiments, the swab strip has a shape of rectangle, square, round, trapezoid, diamond, pentagon, hexagon, or other shapes. The lateral area of the swab strip is less than 100 cm$^2$, 50 cm$^2$, 20 cm$^2$, 10 cm$^2$, 5 cm$^2$, 2 cm$^2$, 1 cm$^2$, 0.5 cm$^2$, 0.2 cm$^2$, 0. cm$^2$, 75 mm$^2$, 50 mm$^2$, 40 mm$^2$, 30 mm$^2$, 20 mm$^2$, 10 mm$^2$, 5 mm$^2$, 4 mm$^2$, 3 mm$^2$, 2 mm$^2$, 1 mm$^2$, 0.5 mm$^2$, or 0.1 mm$^2$, or in a range between any of the two values.

As shown in FIG. 1, the kit 100 of the present disclosure also includes a container 120 that contains a testing medium 122. The container 120 may be any type of bottle, can, flask, pot, jug, cup, pouch, or any apparatus that can be used to withhold and dispense a liquid. In some embodiments, the container 120 is a bottle or pouch. In certain embodiments, the container 120 includes a cap or seal; in certain embodiments, the container 120 is used to directly dispense/deposit the testing medium 122 to a specific location.

The testing medium 122 is configured to perform the testing of the sample. In some embodiments, the testing medium 122 comprises only a liquid (e.g. water) with no particular reagents dissolved therein. In some embodiments, the testing medium 122 comprises buffer pairs or other reagents that are configured to provide an appropriate liquidous environment for the testing, e.g. pH, ionic concentration, and osmotic pressure. In some embodiments, the testing medium 122 comprises a detection agent capable of selectively binding to a target analyte in the sample 90.

In some embodiments, one or both of the plates comprise, on the respective sample contact area, a capture agent capable of selectively binding to and immobilizing a target analyte in the sample.

In some embodiments, one or both of the plates comprise, on the respective sample contact area, a detection agent that is configured to, upon contacting the testing medium, be dissolved and diffuse in the testing medium, and capable of selectively binding to a target analyte in the sample.

In some embodiments, the detection agent is selected from the group consisting of: dyes, antibodies, peptides, oligonucleotides, oligonucleotide mimetics, nanoparticles of different sizes, and any combination thereof.

In some embodiments, the capture agent is selected from the group consisting of: dyes, antibodies, peptides, oligonucleotides, oligonucleotide mimetics, nanoparticles of different sizes, and any combination thereof.

In some embodiments, the target analyte comprises a molecule (e.g., a protein, peptides, DNA, RNA, other nucleic acids, or other molecule), cells, tissues, viruses, and/or nanoparticles with different shapes.

Figure 2:
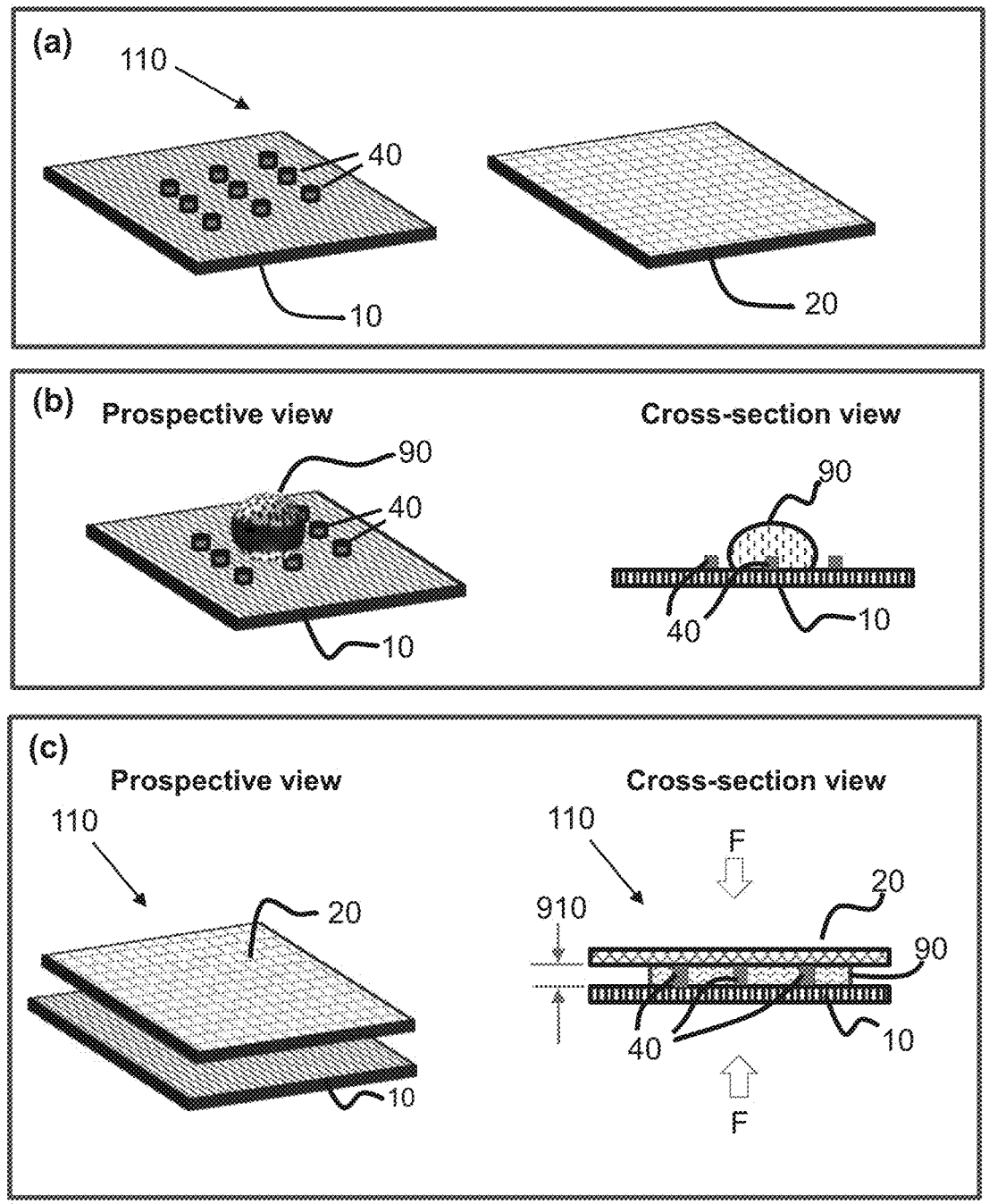
FIG. 2 illustrates an embodiment of a QMAX device.

FIG. 2 illustrates an exemplary embodiment of a QMAX device 110, which comprises a first plate 10, a second plate 20, and spacers 40. The device is termed a QMAX device for "Q" as quantification, "M" as magnifying, "A" as adding reagents, and "X" as acceleration, it is also known as compressed regulated open flow (CROF)), and the process of such is termed as a QMAX process or CORF process. More specifically, panel (A) shows the perspective view of a first plate 10 and a second plate 20 wherein the first plate has spacers 40. It should be noted, however, that the spacers 40 can also be fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also can also be deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform interspacer distance. In the closed configuration, as shown in panel (C) of FIG. 2, the spacing between the plates and the thus the thickness of the sample 902 is regulated by the spacers 40. In some embodiments, the uniform thickness of the sample 902 is substantially similar to the uniform height of the spacers 40. It should be noted that although FIG. 2 shows the spacers 40 to be fixed on one of the plates, in some embodiments the spacers are not fixed. For example, in certain embodiments the spacers are mixed with the sample so that when the sample is compressed into a thin layer, the spacers, which is rigid beads or particles that have a uniform size, regulate the thickness of the sample layer.

Figure 4:
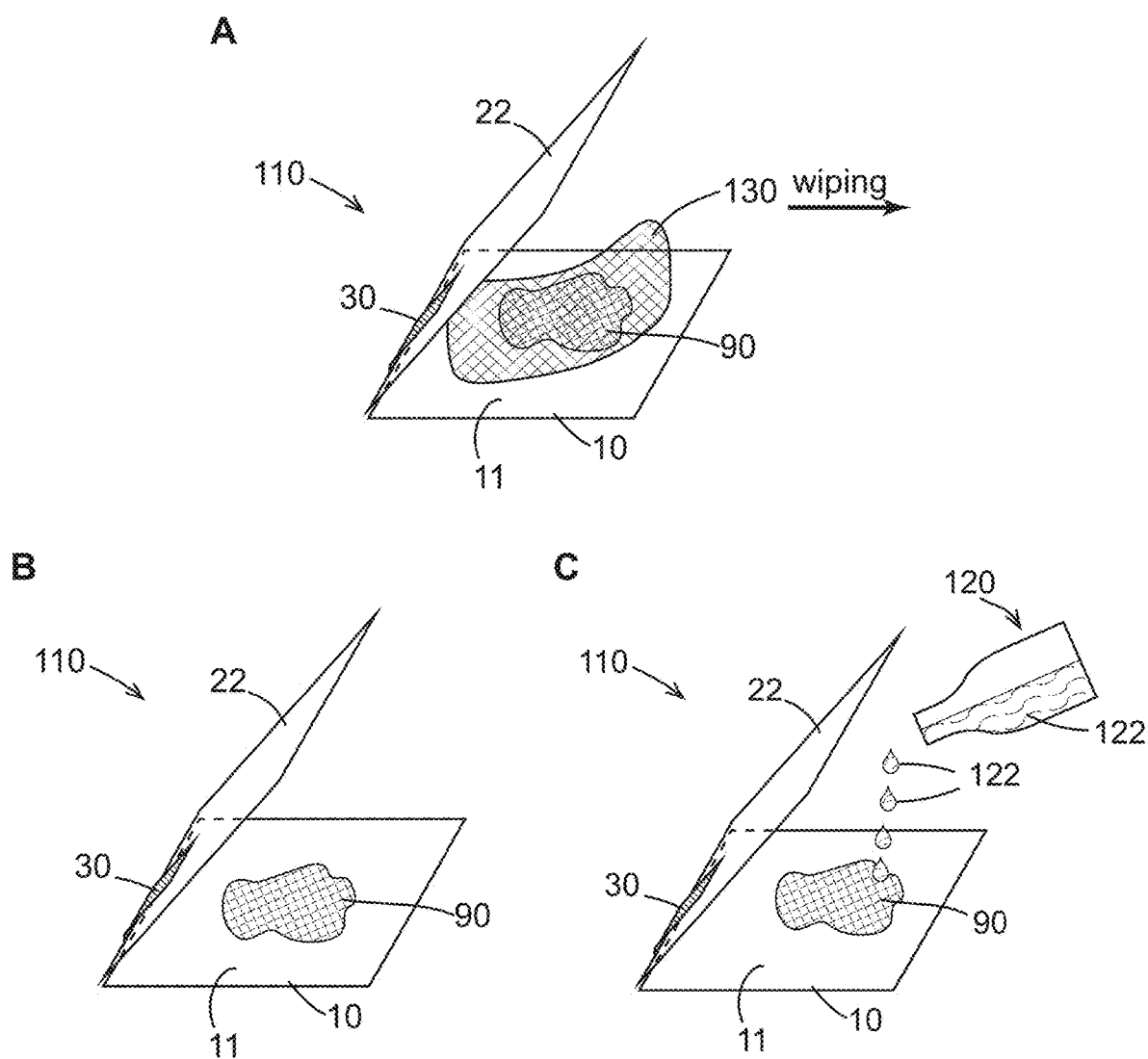
FIG. 4 shows perspective views of the QMAX device in an open configuration when the sample is being transferred and the testing medium is being deposited.

As shown in FIGS. 1 and 4, the first plate 10 and the second plate 20 of the QMAX device 110 are connected by a hinge 30, which allows the first plate 10 and the second plate 20 to pivot against each other. It should be noted that the specific design of the QMAX device 110 may vary. For example, in some embodiments, the QMAX device 110 comprises the first plate 10 and the second plate 20 that not connected by any structure in an open configuration; the hinge 30 may be optional. In addition, the specific design of the hinge 30 may vary; while FIGS. 1 and 4 shows that the hinge 30 covers the aligned edges of the first plate 10 and the second plate 20, the positioning and connection of the hinge 30 may be changed as long as the first plate 10 and the second plate 20 can be switched between an open configuration and a closed configuration, in which inner surfaces of the two plates face each other and are capable of compressing a sample into a thin layer.

In some embodiments, one or both of the plates further comprise, on the respective sample contact area, reagent(s) for bio/chemical processing, preservation, reactions, and/or assay of the sample.

The exemplary embodiments herein disclosed can be combined with the bio/chemical devices and assays including, but not limited to, the devices and assays as disclosed, described, and/or referred to in the following applications:

PCT Application No. PCT/US2016/045437, which was filed on Aug. 10, 2016,

PCT Application No. PCT/US2016/051775, which was filed on Sep. 14, 2016,

PCT Application No. PCT/US2016/051794, which was filed on Sep. 14, 2016,

U.S. Provisional Application No. 62/369,181, which was filed on Jul. 31, 2016,

U.S. Provisional Application No. 62/412,006, which was filed on Oct. 24, 2016,

U.S. Provisional Application No. 62/437,339, which was filed on Dec. 21, 2016,

U.S. Provisional Application No. 62/431,639, which was filed on Dec. 9, 2016,

U.S. Provisional Application No. 62/456,065, which was filed on Feb. 7, 2017,

U.S. Provisional Application No. 62/456,488, which was filed on Feb. 8, 2017,

U.S. Provisional Application No. 62/456,287, which was filed on Feb. 8, 2017,

U.S. Provisional Application No. 62/456,528, which was filed on Feb. 8, 2017,

U.S. Provisional Application No. 62/456,537, which was filed on Feb. 8, 2017,
U.S. Provisional Application No. 62/456,612, which was filed on Feb. 8, 2017,
U.S. Provisional Application No. 62/456,631, which was filed on Feb. 8, 2017,
U.S. Provisional Application No. 62/456,596, which was filed on Feb. 8, 2017,
U.S. Provisional Application No. 62/456,590, which was filed on Feb. 8, 2017,
U.S. Provisional Application No. 62/456,638, which was filed on Feb. 8, 2017,
U.S. Provisional Application No. 62/456,598, which was filed on Feb. 8, 2017,
U.S. Provisional Application No. 62/456,552, which was filed on Feb. 8, 2017,
U.S. Provisional Application No. 62/456,603, which was filed on Feb. 8, 2017,
U.S. Provisional Application No. 62/456,585, which was filed on Feb. 8, 2017,
U.S. Provisional Application No. 62/456,628, which was filed on Feb. 8, 2017,
U.S. Provisional Application No. 62/456,504, which was filed on Feb. 8, 2017,
U.S. Provisional Application No. 62/456,988, which was filed on Feb. 9, 2017,
U.S. Provisional Application No. 62/457,084, which was filed on Feb. 9, 2017,
U.S. Provisional Application No. 62/457,031, which was filed on Feb. 9, 2017,
U.S. Provisional Application No. 62/456,904, which was filed on Feb. 9, 2017,
U.S. Provisional Application No. 62/457,075, which was filed on Feb. 9, 2017,
U.S. Provisional Application No. 62/457,009, which was filed on Feb. 9, 2017,
U.S. Provisional Application No. 62/457,133, which was filed on Feb. 9, 2017,
U.S. Provisional Application No. 62/457,103, which was filed on Feb. 9, 2017,
U.S. Provisional Application No. 62/459,267, which was filed on Feb. 15, 2017,
U.S. Provisional Application No. 62/459,303, which was filed on Feb. 15, 2017,
U.S. Provisional Application No. 62/459,337, which was filed on Feb. 15, 2017,
U.S. Provisional Application No. 62/459,232, which was filed on Feb. 15, 2017,
U.S. Provisional Application No. 62/459,160, which was filed on Feb. 15, 2017,
U.S. Provisional Application No. 62/459,972, which was filed on Feb. 16, 2017,
U.S. Provisional Application No. 62/394,753, which was filed on Sep. 15, 2016,
U.S. Provisional Application No. 62/459,496, which was filed on Feb. 15, 2017,
U.S. Provisional Application No. 62/459,554, which was filed on Feb. 15, 2017,
U.S. Provisional Application No. 62/460,047, which was filed on Feb. 16, 2017,
U.S. Provisional Application No. 62/459,598, which was filed on Feb. 15, 2017,
U.S. Provisional Application No. 62/460,083, which was filed on Feb. 16, 2017,
U.S. Provisional Application No. 62/460,076, which was filed on Feb. 16, 2017,
U.S. Provisional Application No. 62/460,062, which was filed on Feb. 16, 2017,
U.S. Provisional Application No. 62/459,920, which was filed on Feb. 16, 2016,
U.S. Provisional Application No. 62/459,577, which was filed on Feb. 15, 2017,
U.S. Provisional Application No. 62/459,602, which was filed on Feb. 15, 2017,
U.S. Provisional Application No. 62/460,069, which was filed on Feb. 16, 2017,
U.S. Provisional Application No. 62/460,088, which was filed on Feb. 16, 2017,
U.S. Provisional Application No. 62/460,091, which was filed on Feb. 16, 2017,
U.S. Provisional Application No. 62/460,757, which was filed on Feb. 18, 2017,
U.S. Provisional Application No. 62/463,578, which was filed on Feb. 24, 2017,
U.S. Provisional Application No. 62/488,684, which was filed on Apr. 21, 2017,
which are all hereby incorporated in reference by their entireties.

The embodiments in these applications herein incorporated can be regarded in combination with one another or as a single invention, rather than as discrete and independent filings. Moreover, the exemplary embodiments disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in the aforementioned applications, all of which are hereby incorporated in reference by their entireties.

Methods of Testing a Sample Collected by a Swab

Another aspect of the present disclosure is to provide methods of testing a sample collected by a swab.

In some embodiments, the method comprises the steps of:
(a) providing a QMAX device, wherein the QMAX device comprises:
  a first plate, a second plate, and spacers, wherein:
    i. the plates are movable relative to each other into different configurations;
    ii. one or both plates are flexible;
    iii. each of the plates has, on its respective inner surface, a sample contact area for contacting a liquid sample to be collected;
    iv. one or both of the plates comprise the spacers that are fixed with a respective plate;
    v. the spacers have a predetermined substantially uniform height and a predetermined inter-spacer-distance; and
    vi. at least one of the spacers is inside the sample contact area;
(b) collecting a sample by swabbing a surface that holds the sample thereon;
(c) when the two plates are in an open configuration, wiping the sample contact area of the first plate with the swab that has the collected sample to transfer at least part of the collected sample onto the first plate, and then depositing a testing medium on one or both of the plates, wherein in the open configuration, the two plates are partially or entirely separated apart;
(d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and (e) testing the sample while the plates are in the closed configuration, wherein the testing medium is configured to test the sample.

Figure 3:
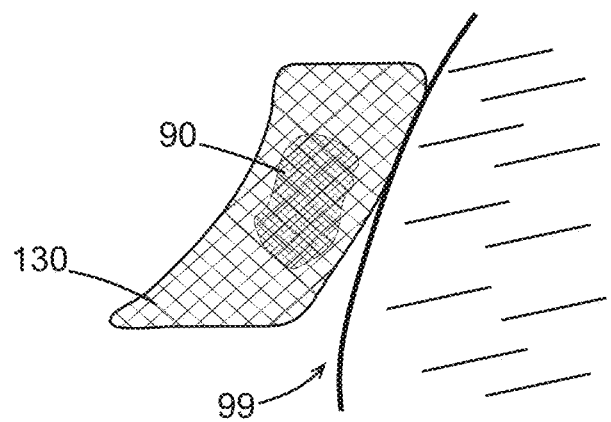
FIG. 3 illustrates a sample collection process in which the swab is used to swab a surface that holds a sample thereon.
Figure 5:
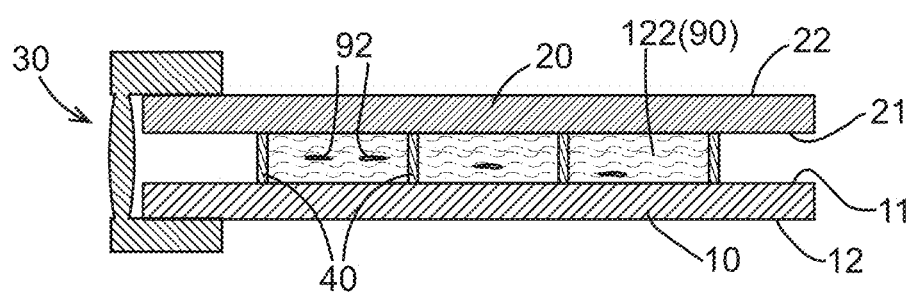
FIG. 5 shows sectional views of QMAX device in the closed configurations after the sample and the testing medium are deposited, when the target analyte is being tested.

FIGS. 3-5 illustrate a process in which the kit 100 of the present disclosure is used to collect and test a sample. In various embodiments, the specific steps in the process may be omitted, augmented, adjusted and/or altered so that the process may be more sensitive, convenient, easy to access, inexpensive, and/or accurate.

FIG. 3 illustrates a sample collection process in which the swab 130 is used to swab a surface 99 that holds the sample 90. The term "swab" as used herein as a verb refers to the action of an entity, actively or passively, passing over a surface of an object with a friction between the surface of the object and the entity, resulting in transfer of certain matters between the object and the entity. In some embodiments, the terms "swab" and "wipe" as used herein as verbs are interchangeable. As shown in the figure, the swabbing action relocates the sample 90 that used to be held on the surface 99 to the swab 120 that passes over the surface with friction. In some embodiments, the swabbing action is performed by an operator of the swab 130. In some embodiments, the swabbing action is completed by the active movement of the surface 99. In some embodiments, the swabbing action is completed by the active movement of both the swab 120 and the surface 99.

The surface 99 that holds the sample thereon, in some embodiments, is a surface of an exterior part of a human or animal body. In some embodiments, the swab is applied to exterior area (e.g. exposed skin) of the body or cavities (e.g. nose, mouth, ear, colon, or vagina) directly accessible from the exterior. In some embodiments, the surface that holds the sample thereon is any solid surface that holds the sample, such as, but not by way of limitation, a testing device surface, a sample collection/transfer apparatus surface, and a solid surface in a criminal scene that contains suspicious bio/chemical traces.

In some embodiments, the body part is a genital (reproductive organ) or areas in close proximity to the genital area of a person. For example, in certain embodiments, the body part is the penis, testicles, scrotum, or skin or cavity (e.g. anus) close to the genital area of a male; in certain embodiments, the body part is the cervix, clitoris, labia, vulva, vagina, or skin or cavity (e.g. anus) close to the genital area of a female. In certain embodiments, the body part is any part of the body where lesions, rashes, nodules, infection sites or body discharges are likely to be located or has been located. For example, in female gonorrhea patients or females suspected of having gonorrhea, the swab may be used to swab the vagina of the subject being tested to collect vaginal fluid as a sample.

It should be noted, in some embodiments, however, the sample collection process is not performed by swabbing or wiping the swab over a solid surface. For instance, in some embodiments, the swab is operated to dip into a reservoir of a liquid sample, and the sample is sucked by the swab through a capillary force due to the structure and material of the swab.

FIG. 4 shows perspective views of the QMAX device 110 in an open configuration when the sample 90 collected on the swab 130 is being transferred onto the first plate 10 and the testing medium 122 is being deposited. Panel (A) shows transferring the sample 90 from the swab 130 to the first plate 10; panel (B) shows that part of the sample 90 is transferred on the first plate 10; and panel (C) shows depositing the testing medium 122 on the first plate 10.

As shown in panel (A) of FIG. 4, the first plate 10 has an inner surface 11 and an outer surface (not shown) and the second plate 20 has an inner surface (not shown) and an outer surface 22. Referring to panels (A) and (B) of FIG. 4, in an open configuration, the first plate 10 and the second plate 20 are partially or entirely separated apart, allowing a sample and/or medium to be deposited on one or both of the plates.

Referring still to FIG. 4 panel (A), the collected sample 90 on the swab 130 is transferred to the first plate 10 by wiping the first plate inner surface 11 with the swab 130 that contains the collected sample 90. The rightward arrow indicates the wiping direction of the swab 130. The wiping action can be certainly in any direction, as long as at least part of the sample 90 is transferred to the first plate 10, as illustrated in panel (B) of FIG. 4, as a result of the friction and/or other forces (e.g. capillary forces) applied by the first plate inner surface 11. The inner surfaces (11 and 21) of the first plate 10 and the second plate 20 respectively include sample contact areas (not marked in FIG. 4) that may occupy a part or an entirety of the inner surfaces. The sample contact areas are for contacting the sample 90. It is to be understood that the swab 130 wipes across at least part of the sample contact area of the first plate 10 and transfers the sample 90 thereto.

Panel (C) of FIG. 4 shows depositing the testing medium 122 to the first plate 10 after the sample 90 is transferred onto the first plate 10. It should be noted, however, the testing medium 122 can be alternatively deposited on the second plate 20, or both the two plates. When the testing medium 122 is deposited on the second plate 20, it can be certainly deposited either before, after, or at the same time as the transfer of the sample 90.

As shown by panel (C) of FIG. 4, the container 120 is used to deposit the testing medium 122 onto the inner surface 11 of the first plate 10. The term "deposit" here means deposit, drip, project, emit, smear or wipe. In some embodiments, the testing medium 122 is deposited directly from the container 120; in other embodiments, a transfer device, e.g. pipette, is used to transfer the testing medium 122 from the container 120 to the specified location, e.g. the inner surface 11 of the first plate 10. In some embodiments, the testing medium 122 is deposited directly by a human hand exerting a force on the container 120. For example, in certain embodiments, the container 120 is a flexible bottle or pouch and a user (e.g. the subject being tested or a person administering the test) may squeeze the container 120 and drip the testing medium 122 to the plate.

The QMAX device 110 may also include spacers (not shown) that control the spacing between the plates when the QMAX device 110 is in a closed configuration, as discussed above and below.

Testing at the Close Configuration

After the sample transfer and the deposition of the testing medium, the QMAX device is thus brought into its closed configuration, in which at least part of the mixture of the sample and the testing medium is compressed by the two plates into a thin layer and the target analyte in the thin layer is being tested/assayed.

FIG. 5 shows a sectional view of the QMAX device in the closed configuration after the sample transfer and the deposition of the testing medium, according to some embodiments. As shown in the figure, the QMAX device comprises a first plate 10, a second plate 20, spacers 40, and a hinge 30. The two plates are connected through the hinge 30 and pivot against each other. In the closed configuration, the mixture 122(90) of the sample 90 and the testing medium 122 is compressed by the two plates into a thin layer, which is confined by the inner surfaces (11 and 21) of the two plates. The thickness of the thin layer is regulated by the spaces 40 and the plates.

In some embodiments, the spacers 40 have a uniform height and a constant inter-spacer distance. In the closed configuration, the mixture 122(90) of the sample 90 and the testing medium 122 is compressed by the two plates in to a layer of uniform thickness, the uniform thickness of the layer is confined by the inner surfaces of the two plates and is regulated by the spacers 40 and the plates. In some embodiments, the uniform thickness of the layer is equal to or about the uniform height of the spacers with a small variation.

In some embodiments, the sample is readily intermiscible with the testing medium, so that the mixture of the sample and the testing medium is a homogeneous solution. In some embodiments, the sample is hardly intermiscible with the testing medium, and the mixture is stratified into different layers. In some embodiments, the testing medium is configured to extract the target analyte from the sample liquid for further bio/chemical assay inside the liquidous environment provided by the testing medium.

As shown in FIG. 5, the target analyte 92 inside the thin layer of the mixture 122(90) is subject to the bio/chemical assay/testing. As discussed above, the testing of the sample can be completed in various forms. In some embodiments, the testing only involves counting of the target analyte 92 inside the thin layer without any treatment of the target analyte 92 or the sample in general. In some embodiments, the testing involves detecting the target analyte 92 by selectively binding a detection agent to the target analyte 92. In some cases, the detection agent is part of the testing medium 122, in other cases, the detection agent is coated on one or both of the plates, and then introduced into the mixture 122(90) by being dissolved into and diffusing in the mixture 122(90), upon contacting the sample 90 or the testing medium 122. In some embodiments, the testing is a sandwich assay where the target analyte is captured and immobilized by a captured agent, and detected by a detection agent. In some embodiments, the capture agent is coated on one or both of the plates.

Examples of Present Disclosure

A1. A test kit for testing a sample collected by a swab, comprising:
  i. a QMAX device, comprising:
    a first plate, a second plate, and spacers, wherein:
      (a) the plates are movable relative to each other into different configurations;
      (b) one or both plates are flexible;
      (c) each of the plates has, on its respective inner surface, a sample contact area for contacting a liquid sample to be collected;
      (d) one or both of the plates comprise the spacers that are fixed with a respective plate;
      (e) the spacers have a predetermined substantially uniform height and a predetermined inter-spacer-distance; and
      (f) at least one of the spacers is inside the sample contact area;
  ii. a swab configured to collect a sample by swabbing a surface that holds the sample thereon; and
  iii. a container that contains a testing medium,
    wherein one of the configurations is an open configuration, in which the two plates are partially or entirely separated apart, at least part of the collected sample on the swab is transferred onto the first plate by wiping the sample contact area of the first plate with the swab that has the collected sample, and the testing medium is deposited on one or both of the plates after the sample transfer;
    wherein another of the configuration is a closed configuration, which is configured after the sample transfer and the deposition of the testing medium; and in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
    wherein testing medium is configured to test the sample.

B1. A method of testing a sample collected by a swab, comprising:
  (a) providing a QMAX device, wherein the QMAX device comprises:
    a first plate, a second plate, and spacers, wherein:
      i. the plates are movable relative to each other into different configurations;
      ii. one or both plates are flexible;
      iii. each of the plates has, on its respective inner surface, a sample contact area for contacting a liquid sample to be collected;
      iv. one or both of the plates comprise the spacers that are fixed with a respective plate;
      v. the spacers have a predetermined substantially uniform height and a predetermined inter-spacer-distance; and
      vi. at least one of the spacers is inside the sample contact area;
  (b) collecting a sample by swabbing a surface that holds the sample thereon;
  (c) when the two plates are in an open configuration, wiping the sample contact area of the first plate with the swab that has the collected sample to transfer at least part of the collected sample onto the first plate, and depositing a testing medium on one or both of the plates, wherein in the open configuration, the two plates are partially or entirely separated apart;
  (d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
  (e) testing the sample while the plates are in the closed configuration, wherein the testing medium is configured to test the sample.

C1. A method of testing a sample collected by a swab, comprising:
  (a) providing a QMAX device, wherein the QMAX device comprises:
    a first plate, a second plate, and spacers, wherein:
      i. the plates are movable relative to each other into different configurations;
      ii. one or both plates are flexible;
      iii. each of the plates has, on its respective inner surface, a sample contact area for contacting a liquid sample to be collected;
      iv. one or both of the plates comprise the spacers that are fixed with a respective plate;
      v. the spacers have a predetermined substantially uniform height and a predetermined inter-spacer-distance; and
      vi. at least one of the spacers is inside the sample contact area;
  (b) collecting a sample by swabbing a surface that holds the sample thereon, wherein the swabbing is performed using a swab, and wherein the swab comprises a sponge;
  (c) when the two plates are in an open configuration, wiping the sample contact area of at least a portion of one or both of the first plate and the second plate with the swab that has the collected sample to transfer at least part of the collected sample onto the first plate, and depositing a testing medium on one or both of the plates, wherein in the open configuration, the two plates are partially or entirely separated apart;
  (d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
  (e) testing the sample while the plates are in the closed configuration, wherein the testing medium is configured to test the sample.

D1. A method of testing a sample collected by a swab, comprising:
  (a) providing a QMAX device, wherein the QMAX device comprises:
    a first plate, a second plate, and spacers, wherein:
      i. the plates are movable relative to each other into different configurations;
      ii. one or both plates are flexible;
      iii. each of the plates has, on its respective inner surface, a sample contact area for contacting a liquid sample to be collected;
      iv. one or both of the plates comprise the spacers that are fixed with a respective plate;
      v. the spacers have a predetermined substantially uniform height and a predetermined inter-spacer-distance; and
      vi. at least one of the spacers is inside the sample contact area;
  (b) collecting a sample by swabbing a surface that holds the sample thereon, wherein the swabbing is performed using a swab, and wherein, prior to swabbing the surface that holds the sample thereon, said swab is (i) contacted with a liquid reagent, and optionally (ii) said swab comprising said liquid reagent is contacted with at least one of the first plate and the second plate;
  (c) when the two plates are in an open configuration, wiping the sample contact area of at least a portion of one or both of the first plate and the second plate with the swab that has the collected sample to transfer at least part of the collected sample onto the first plate, and depositing a testing medium on one or both of the plates, wherein in the open configuration, the two plates are partially or entirely separated apart;
  (d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
  (e) testing the sample while the plates are in the closed configuration, wherein the testing medium is configured to test the sample.

A2. The test kit or method or method of embodiment A1, wherein the swab is a swab strip.

A3. The test kit or method or method of embodiment A1 or A2, wherein the swab comprises a rod and a wad of absorbent material on one end of the rod.

A4. The test kit or method of any prior embodiment, where the testing medium comprises a detection agent capable of selectively binding to a target analyte in the sample.

A5. The test kit or method of any prior embodiment, wherein one or both of the plates comprise, on the respective sample contact area, a capture agent capable of selectively binding to and immobilizing a target analyte in the sample.

A6. The test kit or method of any prior embodiment, wherein one or both of the plates comprise, on the respective sample contact area, a detection agent that is configured to, upon contacting the testing medium, be dissolved and diffuse in the testing medium, and capable of selectively binding to a target analyte in the sample.

A7. The test kit or method of any prior embodiment, wherein the detection agent is selected from the group consisting of: dyes, antibodies, peptides, oligonucleotides, oligonucleotide mimetics, nanoparticles of different sizes, and any combination thereof.

A8. The test kit or method of any prior embodiment, wherein the capture agent is selected from the group consisting of: dyes, antibodies, peptides, oligonucleotides, oligonucleotide mimetics, nanoparticles of different sizes, and any combination thereof.

A9. The test kit or method of any prior embodiment, wherein the target analyte comprises a molecule (e.g., a protein, peptides, DNA, RNA, other nucleic acids, or other molecule), cells, tissues, viruses, and/or nanoparticles with different shapes.

A10. The test kit or method of any prior embodiment, wherein the surface that holds the sample thereon is an exterior part of a human subject or an animal subject.

A11. The test kit or method of any prior embodiment, wherein the surface that holds the sample thereon is a surface of a cavity of a human subject or an animal subject, wherein the cavity is readily accessible from exterior.

A12. The test kit or method of any prior embodiment, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

Sample Collection Without Swab

1. Device and Method for Sample Collection

One aspect of the present disclosure provides a device for collection of a liquid sample from a surface.

In some embodiments, the device comprises a first plate and a plurality of spacers that are fixed to the first plate. In some embodiments, the first plate has a sample contact area for contacting a sample to be collected. In some embodiments, the spacers have a predetermined substantially uniform height and a predetermined inter-spacer-distance. In some embodiments, the spacers and the plate surface that the spacers are fixed on are configured to provide a capillary force that, when the plate with the spacers contacts the sample, attracts at least part of the sample to be deposited on the first plate.

In some embodiments, the device comprises a first plate, a second plate, and spacers. In some embodiments, one or both of the plates are flexible. In some embodiments, each of the plates has, on its respective inner surface, a sample contact area for contacting a sample to be collected. In some embodiments, one or both of the plates comprise the spacers that are fixed with a respective plate. In some embodiments, the spacers have a predetermined substantially uniform height and a predetermined inter-spacer-distance. In some embodiments, at least one of the spacers is inside the sample contact area.

In some embodiments, the plates are movable relative to each other into different configurations. In some embodiments, one of the configurations is an open configuration, in which: the two plates are separated apart, the spacing between the plates is not regulated by the spacers. In some embodiments, another of the configurations is a closed configuration which is configured after the sample deposition in the open configuration; and in the closed configuration: at least part of the deposited sample is compressed by the two plates into a layer of uniform thickness, wherein the uniform thickness of the layer is confined by the inner surfaces of the two plates and is regulated by the plates and the spacers.

In some embodiments, the spacers and the plate surface that the spacers are fixed on are configured to provide a capillary force that, when the plate with the spacers contacts the sample at the open configuration, attracts at least part of the sample to be deposited on the plate.

Another aspect of the present disclosure provides a method for sample collection and sensing.

In some embodiments, the method comprises the steps of:
(a) obtaining a first plate and spacers that are fixed to the first plate, wherein the first plate has a sample contact area for contacting a sample to be collected, and wherein the spacers have a predetermined substantially uniform height and a predetermined inter-spacer-distance; and
(b) contacting a thin layer of liquid sample on a subject surface with the first plate and the spacers, wherein the spacers and the plate surface that the spacers are fixed on are configured to provide a capillary force that attracts at least part of the sample to be deposited on the first plate.

In some embodiments, the method comprises the steps of:
(a) obtaining a first plate, a second plate, and spacers, wherein:
 i. the plates are movable relative to each other into different configurations;
 ii. one or both plates are flexible;
 iii. each of the plates has, on its respective inner surface, a sample contact area for contacting a liquid sample to be collected;
 iv. one or both of the plates comprise the spacers that are fixed with a respective plate;
 v. the spacers have a predetermined substantially uniform height and a predetermined inter-spacer-distance; and
 vi. at least one of the spacers is inside the sample contact area;
(b) contacting a thin layer of liquid sample on a subject surface with the plate that has the spacers fixed thereto when the plates are in an open configuration,
 wherein in the open configuration the two plates are partially or entirely separated apart and the spacing between the plates is not regulated by the spacers; and
 wherein the spacers and the plate surface that the spacers are fixed on are configured to provide a capillary force that, when the plate with the spacers contacts the sample at the open configuration, attracts at least part of the sample to be deposited on the plate; and
(c) after (b), using the two plates to compress at least part of the deposited sample into a layer of substantially uniform thickness that is confined by the sample contact surfaces of the plates, wherein the uniform thickness of the layer is regulated by the spacers and the plates.

Figure 6:
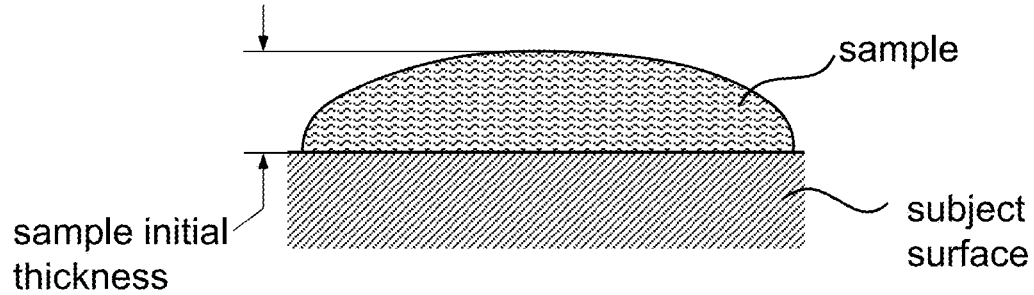
FIG. 6 shows an embodiment of device and method provided by the present disclosure for sample collection and sensing.
Figure 6:
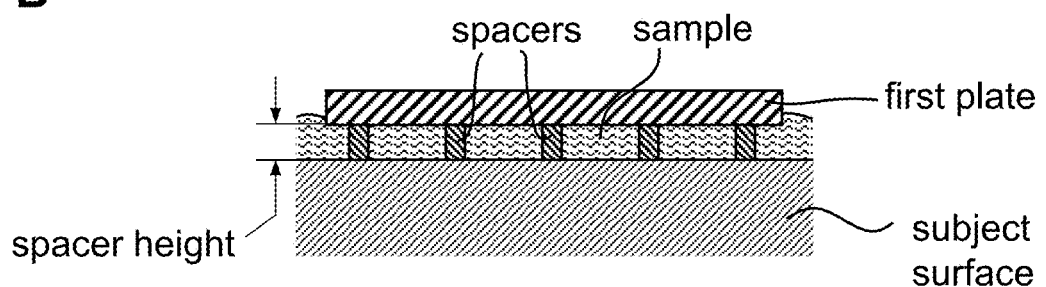
Figure 6:
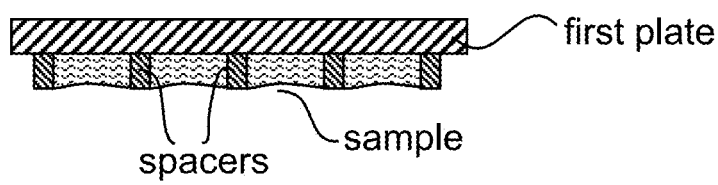
Figure 6:
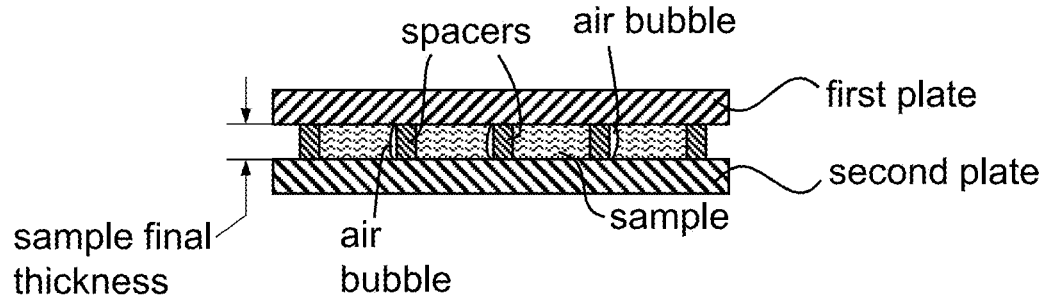

FIG. 6 shows an embodiment of device and method provided by the present disclosure for sample collection and sensing. As discussed above, the device comprises a first plate, a second plate, and spacers. As shown in the figure, the first plate has a plurality of spacers fixed thereon. However, it should be noted that, in some embodiments, the spacers are fixed on the second plate or both the first and second plates. Panel (A) shows a layer of liquid sample that is positioned on a subject surface and has an initial thickness. The sample is to be collected and applied to a device for bio/chemical sensing/assay. Panel (B) shows that the first plate and the spacers are applied against the subject surface and brought into contact with the liquid sample at an open configuration of the two plates. At the open configuration, the two plates are separated apart, and the spacing between the two plates is not regulated by the spacers. Next, for the sample collection, the first plate is separated from the subject surface, as discussed above, the first plate inner surface and the spacers are configured to provide a capillary force that attracts at least part of the sample to be deposited on the first plate. Thus, as shown in panel (C), a portion of the sample is retained on the first plate inner surface in the space between at least a portion of the spacers. After the sample is collected on the first plate, the second plate is brought together with the first plate, and the two plates are compressed against each other to enter a closed configuration. Panel (D) shows the closed configuration of the two plates, where at least part of the deposited sample is compressed by the two plates into a layer of uniform thickness, and the uniform thickness of the layer (or the sample final thickness) is confined by the inner surfaces of the two plates and is regulated by the plates and the spacers.

In some embodiments, the initial thickness of the sample on the subject surface is 0.1 um or less, 0.2 um or less, 0.5 um or less, 1 um or less, 2 um or less, 5 um or less, 10 um or less, 20 um or less, 50 um or less, 100 um or less, 200 um or less, 500 um or less, 1 mm or less, 2 mm or less, 5 mm or less, 10 mm less, or any value in a range between any two of these values. In some preferred embodiments, the initial thickness of the sample on the subject surface is 0.5 um or less, 1 um or less, 2 um or less, 5 um or less, 10 um or less, 20 um or less, 50 um or less, 100 um or less, 200 um or less, 500 um or less, 1 mm or less, 2 mm or less, or any value in a range between any two of these values.

In some embodiments, the subject surface is a skin surface of a subject, such as, but not limited to, a human subject, an animal subject, a plant subject, and any other inanimate subject. In some embodiments, the subject surface is a surface of a device that is used in a laboratory setting, clinical setting, and/or any other appropriate settings. In some embodiments, the subject surface is a surface of a device for sample collection, transportation, processing, assay, and/or any other purposes.

In some embodiments, the sample comprises a bodily fluid such as, but not by way of limitation, amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof. In some embodiments, the subject surface is human skin, and the sample comprises sweat, blood, mucous, and/or semen.

In some embodiments, the contacting of the sample on the surface by the plate with the spacers fixed thereon is a simple direct face-to-face collision between the plate inner surface and the surface that holds the sample thereon. In some embodiments, the contacting comprises a lateral movement along the surface.

In some embodiments, as illustrated in FIG. 6 panel (C), the sample collected on the plate has a surface that is concave between the spacers. It should be noted, however, in some embodiments, the sample collected on the plate has a surface that is either convex in between the spacers, or flat between the spacers, depending on the different surface tension of the sample and the surface wetting properties of the plate inner surface and the spacers.

In some embodiments, as illustrated in FIG. 6 panel (D), there are air bubbles trapped in the sample between the two plates, as a result of the concave surface of the sample shown in FIG. 6 panel (C). It should be noted, however, in some embodiments, there are no air bubbles trapped in the sample between the two plates, for reasons such as, but not limited to, that the sample collected by the plate with spacers has a convex surface or a flat surface.

In some embodiments, the spacers have a uniform height, as indicated in FIG. 6 panel (B), and, as mentioned above, the sample final thickness is regulated by the spacers. In some embodiments, the sample final thickness (or the uniform thickness of the layer) is equal to or approximately the spacer height.

2. Capillary Force for Sample Collection

Figure 7:
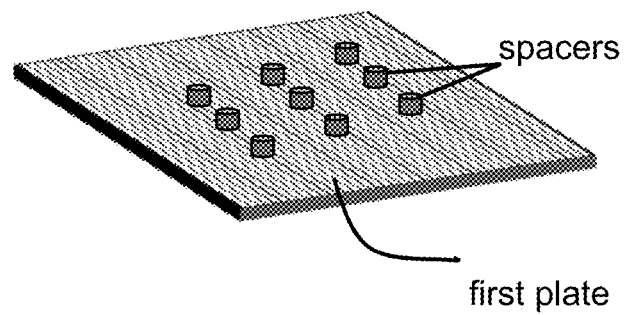
FIG. 7 illustrates an exemplary embodiment of a device for sample collection and sensing according to the present disclosure.
Figure 7:
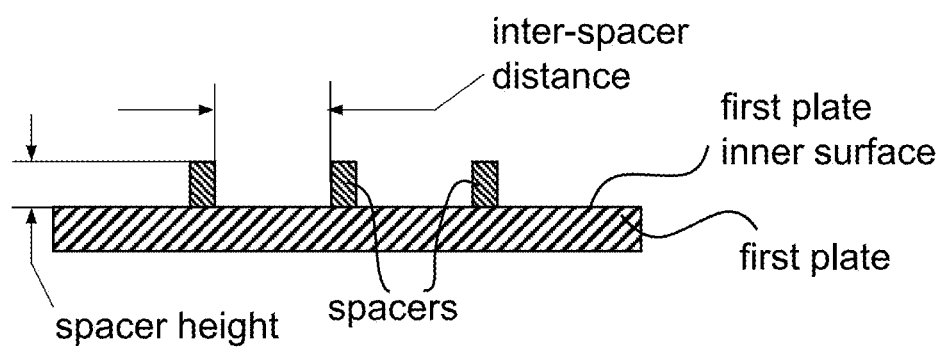

FIG. 7 illustrates an exemplary embodiment of a device for sample collection and sensing according to the present disclosure. The device comprises a first plate, a second plate, and spacers. In this exemplary embodiment, the spacers are fixed to the first plate. Panel (A) shows a perspective view of the first plate and spacers, while panel (B) shows a side view of the same. As shown in the figure, the spacers are aligned in a periodic array with a constant inter-spacer distance. In some embodiments, however, the spacers are aligned in an aperiodic array, that is the inter-spacer distance is not constant across the array. In other embodiments, the spacer array is periodic in some locations of the plate while non-periodic in other locations.

In some embodiments, as discussed above, when the plate with the spacers fixed thereon contacts the sample on the subject surface at the open configuration, the plate surface that the spacers are fixed on and the spacers are configured to provide a capillary force that attracts at least part of the sample to be deposited on the plate. In some embodiments, the wetting properties of the plate inner surface that the spacers fixed thereon and the spacers, the inter-spacer distance, and the spacer height are among many other factors that contribute to such a configuration providing said capillary force.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 $\mu$m or less, 5 $\mu$m or less, 7 $\mu$m or less, 10 $\mu$m or less, 20 $\mu$m or less, 30 $\mu$m or less, 40 $\mu$m or less, 50 $\mu$m or less, 60 $\mu$m or less, 70 $\mu$m or less, 80 $\mu$m or less, 90 $\mu$m or less, 100 $\mu$m or less, 200 $\mu$m or less, 300 $\mu$m or less, 400 $\mu$m or less, or in a range between any two of the values.

In certain embodiments, the inter-spacer distance is at 400 $\mu$m or less, 500 $\mu$m or less, 1 mm or less, 2 mm or less, 3 mm or less, 5 mm or less, 7 mm or less, 10 mm or less, or in any range between the values. In certain embodiments, the inter-spacer distance is 10 mm or less, 20 mm or less, 30 mm or less, 50 mm or less, 70 mm or less, 100 mm or less, or in any range between the values.

In some embodiments, all spacers have the same predetermined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 $\mu$m or less, 2 $\mu$m or less, 3 $\mu$m or less, 5 $\mu$m or less, 10 $\mu$m or less, 20 $\mu$m or less, 30 $\mu$m or less, 50 $\mu$m or less, 100 $\mu$m or less, 150 $\mu$m or less, 200 $\mu$m or less, 300 $\mu$m or less, 500 $\mu$m or less, 800 $\mu$m or less, 1 mm or less, 2 mm or less, 4 mm or less, or in a range between any two of the values.

In some embodiments, a plate has an inner surface that wets (i.e. contact angle is less 90 degree) the sample. In some embodiments, both plates have an inner surface that wets the sample; either with the same or different wettability.

In some embodiments, a plate has an inner surface that wets the sample; and another plate has an inner surface that does not (i.e. the contact angle equal to or larger than 90 degree). The wetting of a plate inner surface refers to a part or the entire area of the plate.

It is to be understood that it is the combinatory effect of the inter-spacer distance, the spacer height, the wetting properties of the plate and the spacers, and many other factors that determine the "attractiveness" to the sample to be collected, so that the sample is collected by the device through a simple direct contact between the plate with spacers and the sample.

3. Device and Method for Sample Sensing

Another aspect of the present disclosure is to provide devices and methods for sample collection and sensing to be performed with a single device, with no need of a separate sample collection or transportation device.

As illustrated in FIG. 6 panel (D), a second plate is used to compress the deposited sample into a thin layer. In some embodiments, the thin layer can be directly subject to bio/chemical sensing by the same device without the need of transferring the sample to a different device. The device is termed a QMAX (Q: quantification; M: magnifying; A: adding reagents; X: acceleration; also known as compressed regulated open flow (CROF)) device, and the process of such is termed as a QMAX process or CORF process.

FIG. 2 shows an embodiment of a generic QMAX device. The generic QMAX device comprises a first plate 10, a second plate 2 and spacers 40. In particular, panel (A) shows the perspective view of a first plate 10 and a second plate 20 wherein the first plate has spacers 40. It should be noted, however, that the spacers 40 can also be fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also can also be deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform inter-spacer distance. In the closed configuration, as shown in panel (C) of FIG. 6, the spacing between the plates and the thus the thickness of the sample 90 is regulated by the spacers 40. In some embodiments, the uniform thickness of the sample 90 is substantially similar to the uniform height of the spacers 40. It should be noted that although FIG. 2 shows the spacers 40 to be fixed on one of the plates, in some embodiments the spacers are not fixed. For example, in certain embodiments the spacers are mixed with the sample so that when the sample is compressed into a thin layer, the spacers, which is rigid beads or particles that have a uniform size, regulate the thickness of the sample layer.

Additional Examples of Present Disclosure

A1. A device for sample collection and sensing, comprising: a first plate, a second plate, and spacers, wherein:
i. the plates are movable relative to each other into different configurations;
ii. one or both plates are flexible;
iii. each of the plates has, on its respective inner surface, a sample contact area for contacting a liquid sample to be collected;
iv. one or both of the plates comprise the spacers that are fixed with a respective plate;
v. the spacers have a predetermined substantially uniform height and a predetermined inter-spacer-distance; and
vi. at least one of the spacers is inside the sample contact area;
wherein one of the configurations is an open configuration, in which: the two plates are separated apart, the spacing between the plates is not regulated by the spacers;
wherein the spacers and the plate surface that the spacers are fixed on are configured to provide a capillary force that, when the plate with the spacers contacts the sample at the open configuration, attracts at least part of the sample to be deposited on the plate; and
wherein another of the configurations is a closed configuration which is configured after the sample deposition in the open configuration; and in the closed configuration: at least part of the deposited sample is compressed by the two plates into a layer of uniform thickness, wherein the uniform thickness of the layer is confined by the inner surfaces of the two plates and is regulated by the plates and the spacers.

AA1. A device for sample collection and sensing, comprising a first plate and a plurality of spacers that are fixed to the first plate, wherein the first plate has a sample contact area for contacting a sample to be collected, wherein the spacers have a predetermined substantially uniform height and a predetermined inter-spacer-distance, and wherein the spacers and the plate surface that the spacers are fixed on are configured to provide a capillary force that, when the plate with the spacers contacts the sample, attracts at least part of the sample to be deposited on the first plate.

B1. A method of sample collection and sensing, comprising the steps of:
(a) obtaining a first plate, a second plate, and spacers, wherein:
i. the plates are movable relative to each other into different configurations;
ii. one or both plates are flexible;
iii. each of the plates has, on its respective inner surface, a sample contact area for contacting a liquid sample to be collected;
iv. one or both of the plates comprise the spacers that are fixed with a respective plate;
v. the spacers have a predetermined substantially uniform height and a predetermined inter-spacer-distance; and
vi. at least one of the spacers is inside the sample contact area;
(b) contacting a thin layer of liquid sample on a subject surface with the plate that has the spacers fixed thereto when the plates are in an open configuration,
wherein in the open configuration the two plates are partially or entirely separated apart and the spacing between the plates is not regulated by the spacers; and
wherein the spacers and the plate surface that the spacers are fixed on are configured to provide a capillary force that, when the plate with the spacers contacts the sample at the open configuration, attracts at least part of the sample to be deposited on the plate; and (c) after (b), using the two plates to compress at least part of the deposited sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers;

wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

BB1. A method of sample collection and sensing, comprising the steps of:

(a) obtaining a first plate and spacers that are fixed to the first plate, wherein the first plate has a sample contact area for contacting a sample to be collected, and wherein the spacers have a predetermined substantially uniform height and a predetermined inter-spacer-distance; and (b) contacting a thin layer of liquid sample on a subject surface with the first plate and the spacers, wherein the spacers and the plate surface that the spacers are fixed on are configured to provide a capillary force that attracts at least part of the sample to be deposited on the first plate.

AB (Device and Method)

The device or method of any prior embodiment, wherein one or both of the plates further comprise, on the respective sample contact area, reagent for a bio/chemical assay of the sample.

The device or method of any prior embodiment, wherein one or both of the plates further comprise, on the respective sample contact area, reagent for processing the sample.

The device or method of any prior embodiment, wherein one or both of the plates further comprise, on the respective sample contact area, reagent for preserving the sample.

The method of any prior method embodiment, wherein the sample comprises sweat.

The method of any prior method embodiment, wherein the sample comprises blood.

The method of any prior method embodiment, wherein the sample comprises mucous.

The method of any prior method embodiment, wherein the sample comprises a bodily fluid selected from the group consisting of: amniotic fluid, aqueous humour, vitreous humour, blood, e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

The method of any prior method embodiment, wherein the sample is an environmental sample from an environmental source selected from the group consisting of a river, lake, pond, ocean, glaciers, icebergs, rain, snow, sewage, reservoirs, tap water, drinking water, etc.; solid samples from soil, compost, sand, rocks, concrete, wood, brick, sewage, the air, underwater heat vents, industrial exhaust, vehicular exhaust and any combination thereof.

The method of any prior method embodiment, wherein the sample is a foodstuff sample selected from the group consisting of: raw ingredients, cooked food, plant and animal sources of food, preprocessed food, partially or fully processed food, and any combination thereof.

Related Documents

The present disclosure includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $\frac{1}{1000}$, $\frac{1}{100}$, $\frac{1}{100}$, $\frac{1}{5}$, $\frac{1}{2}$ of the spacer height or in a range of any two values, and in either protrusion or well form.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the present disclosure includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

1. Samples

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu L$, also "uL" herein) or less, 500 $\mu L$ or less, 300 $\mu L$ or less, 250 $\mu L$ or less, 200 $\mu L$ or less, 170 $\mu L$ or less, 150 $\mu L$ or less, 125 $\mu L$ or less, 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values.

In some embodiments, the volume of the sample includes, but is not limited to, about 100 µL or less, 75 µL or less, 50 µL or less, 25 µL or less, 20 µL or less, 15 µL or less, 10 µL or less, 5 µL or less, 3 µL or less, 1 µL or less, 0.5 µL or less, 0.1 µL or less, 0.05 µL or less, 0.001 µL or less, 0.0005 µL or less, 0.0001 µL or less, 10 pL or less, 1 pL or less, or a range between any two of the values. In some embodiments, the volume of the sample includes, but is not limited to, about 10 µL or less, 5 µL or less, 3 µL or less, 1 µL or less, 0.5 µL or less, 0.1 µL or less, 0.05 µL or less, 0.001 µL or less, 0.0005 µL or less, 0.0001 µL or less, 10 pL or less, 1 pL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

2. Applications

The devices, apparatus, systems, and methods herein disclosed can be used in various types of biological/chemical sampling, sensing, assays and applications, which include the applications listed, described and/or summarized in PCT Application (designating U.S.) No. PCT/US2016/045437, which was filed on Aug. 10, 2016, and is hereby incorporated by reference by its entirety.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present disclosure include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained. In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

3. Analytes, Biomarkers, and Diseases

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present disclosure include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured amount of the analyte in the sample can be diagnostic of a disease or a condition.

In any embodiment, the devices, apparatus, systems, and methods in the present disclosure can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present disclosure.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipette, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

4. Labels

The devices, apparatus, systems, and methods herein disclosed can be used with various types of labels, which include the labels disclosed, described and/or summarized in PCT Application (designating U.S.) No. PCT/US2016/045437, which was filed on Aug. 10, 2016, and is hereby incorporated by reference by its entirety.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminonylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

5. QMAX Device

The devices, apparatus, systems, and methods herein disclosed can include or use a QMAX device ((Q: quantification; M: magnifying; A: adding reagents; X: acceleration; also known as Q-card in some embodiments or compressed regulated open flow (CROF) device), which include the QMAX device listed, described and/or summarized in PCT Application (designating U.S.) Nos. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

As used here, the terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX card.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present disclosure intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

6. Spacers

The devices, apparatus, systems, and methods herein disclosed can include or use a device (e.g. a QMAX device), which comprises spacers that are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

7. Adaptor

The devices, apparatus, systems, and methods herein disclosed can be used with an adaptor, which is configured to accommodate the device and connect the device to a reader, such as but not limited to a smartphone. In some embodiments, the Q-cards are used together with sliders that allow the card to be inserted into the adaptor so that the card can be read by a smartphone detection system. The structure, material, function, variation, dimension and connection of the Q-card, the sliders, and the adaptor are disclosed, listed, described, and/or summarized in PCT Application (designating U.S.) Nos. PCT/US2016/045437 filed on Aug. 10, 2016 and PCT/US0216/051775 filed on Sep. 14, 2016, U.S. Provisional Application No. 62/456,590 filed on Feb. 8, 2017, 62/459,554 filed on Feb. 15, 2017, and 62/460,075 filed on Feb. 8, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample. The structures, functions, and configurations of the optical components in some embodiments can be found in PCT Application (designating U.S.) Nos. PCT/US2016/045437 filed on Aug. 10, 2016 and PCT/US0216/051775 filed on Sep. 14, 2016, U.S. Provisional Application Nos. 62/456,590 filed on Feb. 8, 2017, 62/459,554 filed on Feb. 15, 2017, and 62/460,075 filed on Feb. 8, 2017, all of which applications are incorporated herein in their entireties for all purposes.

8. Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
|---|---|---|
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |

Plates:

| Parameters | Embodiments | Preferred Embodiments |
|---|---|---|
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm²; or around 750 mm². |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
|---|---|---|
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm² or less, 5 mm² or less, 10 mm² or less, 20 mm² or less, 30 mm² or less, 40 mm² or less, 50 mm² or less, 100 mm² or less, 200 mm² or less, 500 mm² or less, or in a range between any of the two values | In the range of 20 to 200 mm²; or about 120 mm² |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, | In the range of 90 to 180 degrees |

Hinge:

| Parameters | Embodiments | Preferred Embodiments |
|---|---|---|
| | 225 or less, 240 or less, 255 or less, 270 or less, 285 or less, 300 or less, 315 or less, 330 or less, 345 or less or 360 or less degrees, or in a range between any two of these values | |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 mm$^2$ (square millimeter) or less, 10 mm$^2$ or less, 25 mm$^2$ or less, 50 mm$^2$ or less, 75 mm$^2$ or less or in a range between any two of these values. | In the range of 10 to 150 mm$^2$; or about 50 mm$^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |

Trench:

| Parameters | Embodiments | Preferred Embodiments |
|---|---|---|
| Cross-sectional Area | 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values. | |

9. Hand Pressing

For the devices, apparatus, systems, and methods herein disclosed, human hands can be used for manipulating or handling or the plates and/or samples. In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

10. Smartphone

The devices, apparatus, systems, and methods herein disclosed can be used with a mobile device, such as but not limited to a smartphone. The smartphone detection technology is herein disclosed, or listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

11. Cloud

The devices, apparatus, systems, and methods herein disclosed can be used with cloud storage and computing technologies. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed is:

1. A method of testing a sample collected by a swab, comprising:
   (a) providing a QMAX device, wherein the QMAX device comprises:
      a first plate, a second plate, and spacers, wherein:
         i. the plates are movable relative to each other into different configurations;
         ii. one or both plates are flexible;
         iii. each of the plates has, on its respective inner surface, a sample contact area for contacting a liquid sample to be collected;
         iv. one or both of the plates comprise the spacers that are fixed to a respective plate;
         v. the spacers have a predetermined substantially uniform height and a predetermined inter-spacer-distance; and
         vi. at least one of the spacers is inside the sample contact area;
   (b) collecting a sample by swabbing a surface that holds the sample thereon, wherein the swabbing is performed using a swab, and wherein the swab comprises an absorbent material;
   (c) when the two plates are in an open configuration, wiping the sample contact area of at least a portion of one or both of the first plate and the second plate with the swab that has the collected sample to transfer at least part of the collected sample onto the first plate, and depositing a testing medium on one or both of the plates, wherein in the open configuration, the two plates are partially or entirely separated apart;
   (d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
   (e) testing the sample while the plates are in the closed configuration, wherein the testing medium is configured to test the sample.

2. The method of claim 1, wherein the swab is a swab strip.

3. The method of claim 1, wherein the swab comprises a rod and a wad of absorbent material on one end of the rod.

4. The method of claim 1, where the testing medium comprises a detection agent capable of selectively binding to a target analyte in the sample.

5. The method of claim 4, wherein the detection agent is selected from the group consisting of: dyes, antibodies, peptides, oligonucleotides, oligonucleotide mimetics, nanoparticles of different sizes, and any combination thereof.

6. The method of claim 4, wherein the target analyte comprises a molecule (e.g., a protein, peptides, DNA, RNA, other nucleic acids, or other molecule), cells, tissues, viruses, and/or nanoparticles with different shapes.

7. The method of claim 1, wherein one or both of the plates comprise, on the respective sample contact area, a capture agent capable of selectively binding to and immobilizing a target analyte in the sample.

8. The method of claim 7, wherein the capture agent is selected from the group consisting of: dyes, antibodies, peptides, oligonucleotides, oligonucleotide mimetics, nanoparticles of different sizes, and any combination thereof.

9. The method of claim 1, wherein one or both of the plates comprise, on the respective sample contact area, a detection agent that is configured to, upon contacting the testing medium, be dissolved and diffuse in the testing medium, and capable of selectively binding to a target analyte in the sample.

10. The method of claim 1, wherein the surface that holds the sample thereon is an exterior part of a human subject or an animal subject.

11. The method of claim 1, wherein the surface that holds the sample thereon is a surface of a cavity of a human subject or an animal subject, wherein the cavity is readily accessible from exterior.

12. The method of claim 1, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

13. A method of testing a collected sample, comprising:
(a) providing a QMAX device, wherein the QMAX device comprises:
a first plate, a second plate, and spacers, wherein:
  i. the plates are movable relative to each other into different configurations;
  ii. one or both plates are flexible;
  iii. each of the plates has, on its respective inner surface, a sample contact area for contacting a liquid sample to be collected;
  iv. one or both of the plates comprise the spacers that are fixed to a respective plate;
  v. the spacers have a predetermined substantially uniform height and a predetermined inter-spacer-distance; and
  vi. at least one of the spacers is inside the sample contact area;
(b) collecting a sample by swabbing a surface that holds the sample thereon, wherein the swabbing is performed using at least one surface of a plate of the QMAX device having the sample contact area, and wherein, prior to swabbing the surface that holds the sample thereon, the at least one surface of a plate of the QMAX device having the sample contact area is contacted with a liquid reagent;
(c) depositing a testing medium on one or both of the plates, wherein one or both plates are in an open configuration, and the two plates are partially or entirely separated apart;
(d) after step (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
(e) testing the sample while the plates are in the closed configuration, wherein the testing medium is configured to test the sample.

14. The method of claim 13, where the testing medium comprises a detection agent capable of selectively binding to a target analyte in the sample.

15. The method of claim 14, wherein the detection agent is selected from the group consisting of: dyes, antibodies, peptides, oligonucleotides, oligonucleotide mimetics, nanoparticles of different sizes, and any combination thereof.

16. The method of claim 14, wherein the target analyte comprises a molecule (e.g., a protein, peptides, DNA, RNA, other nucleic acids, or other molecule), cells, tissues, viruses, and/or nanoparticles with different shapes.

17. The method of claim 13, wherein one or both of the plates comprise, on the respective sample contact area, a capture agent capable of selectively binding to and immobilizing a target analyte in the sample.

18. The method of claim 17, wherein the capture agent is selected from the group consisting of: dyes, antibodies, peptides, oligonucleotides, oligonucleotide mimetics, nanoparticles of different sizes, and any combination thereof.

19. The method of claim 13, wherein one or both of the plates comprise, on the respective sample contact area, a detection agent that is configured to, upon contacting the testing medium, be dissolved and diffuse in the testing medium, and capable of selectively binding to a target analyte in the sample.

20. The method of claim 13, wherein the surface that holds the sample thereon is an exterior part of a human subject or an animal subject.

21. The method of claim 13, wherein the surface that holds the sample thereon is a surface of a cavity of a human subject or an animal subject, wherein the cavity is readily accessible from exterior.

22. The method of claim 13, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

23. A method of testing a sample collected by a swab, comprising:
(a) providing a QMAX device, wherein the QMAX device comprises:
a first plate, a second plate, and spacers, wherein:
  i. the plates are movable relative to each other into different configurations;

ii. one or both plates are flexible;
iii. each of the plates has, on its respective inner surface, a sample contact area for contacting a liquid sample to be collected;
iv. one or both of the plates comprise the spacers that are fixed to a respective plate;
v. the spacers have a predetermined substantially uniform height and a predetermined inter-spacer-distance; and
vi. at least one of the spacers is inside the sample contact area;

(b) collecting a sample by swabbing a surface that holds the sample thereon with a swab;

(c) when the two plates are in an open configuration, wiping the sample contact area of the first plate with the swab that has the collected sample to transfer at least part of the collected sample onto the first plate, and without depositing a testing medium on one or both of the plates, wherein in the open configuration, the two plates are partially or entirely separated apart;

(d) after step (c), bringing the two plates together and pressing the plates into a closed configuration, wherein in the closed configuration: at least part of the collected sample on the first plate is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and (e) testing the sample while the plates are in the closed configuration, wherein the testing medium is configured to test the sample.

24. The method of claim 23, wherein the swab is a swab strip.

25. The method of claim 23, wherein the swab comprises a rod and a wad of absorbent material on one end of the rod.

26. The method of claim 23, wherein one or both of the plates comprise, on the respective sample contact area, a capture agent capable of selectively binding to and immobilizing a target analyte in the sample.

27. The method of claim 26, wherein the capture agent is selected from the group consisting of: dyes, antibodies, peptides, oligonucleotides, oligonucleotide mimetics, nanoparticles of different sizes, and any combination thereof.

28. The method of claim 26, wherein the target analyte comprises a molecule (e.g., a protein, peptides, DNA, RNA, other nucleic acids, or other molecule), cells, tissues, viruses, and/or nanoparticles with different shapes.

29. The method of claim 23, wherein one or both of the plates comprise, on the respective sample contact area, a detection agent that is configured to, upon contacting the testing medium, be dissolved and diffuse in the testing medium, and capable of selectively binding to a target analyte in the sample.

30. The method of claim 29, wherein the detection agent is selected from the group consisting of: dyes, antibodies, peptides, oligonucleotides, oligonucleotide mimetics, nanoparticles of different sizes, and any combination thereof.

31. The method of claim 23, wherein the surface that holds the sample thereon is an exterior part of a human subject or an animal subject.

32. The method of claim 23, wherein the surface that holds the sample thereon is a surface of a cavity of a human subject or an animal subject, wherein the cavity is readily accessible from exterior.

33. The method of claim 23, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

34. A test kit for testing a sample collected by a swab, comprising:
i. a QMAX device, comprising:
a first plate, a second plate, and spacers, wherein:
(a) the plates are movable relative to each other into different configurations;
(b) one or both plates are flexible;
(c) each of the plates has, on its respective inner surface, a sample contact area for contacting a liquid sample to be collected;
(d) one or both of the plates comprise the spacers that are fixed to a respective plate;
(e) the spacers have a predetermined substantially uniform height and a predetermined inter-spacer-distance; and
(f) at least one of the spacers is inside the sample contact area;
ii. a swab configured to collect a sample by swabbing a surface that holds the sample thereon; and
iii. a container that contains a testing medium;
wherein one of the configurations is an open configuration, in which the two plates are partially or entirely separated apart, at least part of the collected sample on the swab is transferred onto the first plate by wiping the sample contact area of the first plate with the swab that has the collected sample, and the testing medium is deposited on one or both of the plates after the sample transfer;
wherein another of the configuration is a closed configuration, which is configured after the sample transfer and the deposition of the testing medium; and in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
wherein testing medium is configured to test the sample.

35. The test kit of claim 34, wherein the swab is a swab strip.

36. The test kit of claim 34, wherein the swab comprises a rod and a wad of absorbent material on one end of the rod.

37. The test kit of claim 34, where the testing medium comprises a detection agent capable of selectively binding to a target analyte in the sample.

38. The test kit of claim 37, wherein the detection agent is selected from the group consisting of: dyes, antibodies, peptides, oligonucleotides, oligonucleotide mimetics, nanoparticles of different sizes, and any combination thereof.

39. The test kit of claim 37, wherein the target analyte comprises a molecule (e.g., a protein, peptides, DNA, RNA, other nucleic acids, or other molecule), cells, tissues, viruses, and/or nanoparticles with different shapes.

40. The test kit of claim 34, wherein one or both of the plates comprise, on the respective sample contact area, a capture agent capable of selectively binding to and immobilizing a target analyte in the sample.

41. The test kit of claim 40, wherein the capture agent is selected from the group consisting of: dyes, antibodies, peptides, oligonucleotides, oligonucleotide mimetics, nanoparticles of different sizes, and any combination thereof.

42. The test kit of claim 34, wherein one or both of the plates comprise, on the respective sample contact area, a detection agent that is configured to, upon contacting the testing medium, be dissolved and diffuse in the testing medium, and capable of selectively binding to a target analyte in the sample.

43. The test kit of claim 34, wherein the surface that holds the sample thereon is an exterior part of a human subject or an animal subject.

44. The test kit of claim 34, wherein the surface that holds the sample thereon is a surface of a cavity of a human subject or an animal subject, wherein the cavity is readily accessible from exterior.

45. The test kit of claim 34, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

46. A method of testing a sample collected by a swab, comprising:
  (a) providing a QMAX device, wherein the QMAX device comprises:
    a first plate, a second plate, and spacers, wherein:
      i. the plates are movable relative to each other into different configurations;
      ii. one or both plates are flexible;
      iii. each of the plates has, on its respective inner surface, a sample contact area for contacting a liquid sample to be collected;
      iv. one or both of the plates comprise the spacers that are fixed to a respective plate;
      v. the spacers have a predetermined substantially uniform height and a predetermined inter-spacer-distance; and
      vi. at least one of the spacers is inside the sample contact area;
  (b) collecting a sample by swabbing a surface that holds the sample thereon with a swab;
  (c) when the two plates are in an open configuration, wiping the sample contact area of the first plate with the swab that has the collected sample to transfer at least part of the collected sample onto the first plate, and depositing a testing medium on one or both of the plates, wherein in the open configuration, the two plates are partially or entirely separated apart;
  (d) after steps (c), bringing the two plates together and pressing the plates into a closed configuration, wherein in the closed configuration: at least part of the deposited testing medium is compressed by the two plates into a layer of uniform thickness, and at least part of the transferred sample is inside the layer of uniform thickness, wherein the uniform thickness of the layer is confined by the inner surfaces of the two plates and is regulated by the plates and the spacers; and
  (e) testing the sample while the plates are in the closed configuration, wherein the testing medium is configured to test the sample.

47. The method of claim 46, wherein the swab is a swab strip.

48. The method of claim 46, wherein the swab comprises a rod and a wad of absorbent material on one end of the rod.

49. The method of claim 46, where the testing medium comprises a detection agent capable of selectively binding to a target analyte in the sample.

50. The method of claim 49, wherein the detection agent is selected from the group consisting of: dyes, antibodies, peptides, oligonucleotides, oligonucleotide mimetics, nanoparticles of different sizes, and any combination thereof.

51. The method of claim 49, wherein the target analyte comprises a molecule (e.g., a protein, peptides, DNA, RNA, other nucleic acids, or other molecule), cells, tissues, viruses, and/or nanoparticles with different shapes.

52. The method of claim 46, wherein one or both of the plates comprise, on the respective sample contact area, a capture agent capable of selectively binding to and immobilizing a target analyte in the sample.

53. The method of claim 52, wherein the capture agent is selected from the group consisting of: dyes, antibodies, peptides, oligonucleotides, oligonucleotide mimetics, nanoparticles of different sizes, and any combination thereof.

54. The method of claim 46, wherein one or both of the plates comprise, on the respective sample contact area, a detection agent that is configured to, upon contacting the testing medium, be dissolved and diffuse in the testing medium, and capable of selectively binding to a target analyte in the sample.

55. The method of claim 46, wherein the surface that holds the sample thereon is an exterior part of a human subject or an animal subject.

56. The method of claim 46, wherein the surface that holds the sample thereon is a surface of a cavity of a human subject or an animal subject, wherein the cavity is readily accessible from exterior.

57. The method of claim 46, wherein the sample comprises a bodily fluid selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

* * * * *